United States Patent [19]

Poole et al.

[11] Patent Number: 4,997,651

[45] Date of Patent: Mar. 5, 1991

[54] PHARMACEUTICAL FORMULATIONS

[76] Inventors: Stephen W. Poole; Timothy P. Stanley; Geoffrey Divall; Terence W. Packham; Joseph Knight, all of The Wellcome Foundation Limited, Temple Hill, Dartford, England

[21] Appl. No.: 273,227

[22] Filed: Nov. 18, 1988

[30] Foreign Application Priority Data

Nov. 19, 1987 [GB] United Kingdom ............... 8727157

[51] Int. Cl.$^5$ .............................................. A61K 9/14
[52] U.S. Cl. ..................................... 424/422; 424/80; 424/489; 424/501
[58] Field of Search .................... 424/489, 85.91, 422, 424/80, 501

[56] References Cited

U.S. PATENT DOCUMENTS

| 3,032,584 | 5/1962 | Bergel et al. | 260/518 |
| 3,032,585 | 5/1962 | Bergel et al. | 260/518 |
| 4,029,778 | 6/1977 | Fex et al. | 514/178 |
| 4,738,843 | 4/1988 | Oguchi et al. | 514/8 |

FOREIGN PATENT DOCUMENTS

| 0212853 | 3/1987 | European Pat. Off. |
| 2285855 | 4/1976 | France |

OTHER PUBLICATIONS

Martindale, The Extra Pharmacopoeia, Twenty-eight Edition, 1982, p. 213.
British Pharmacopoeia 1988, vol. I, p. 356.
The United States Pharmacopoeia, 1985, pp. 630–631.
ABPI Data Sheet Compendium, 1986–1987, pp. 309–310.
Rote Liste, 1987 Editio Cantor, Aulendorf/Wurtt. DE.
J. of Pharm. Sci., vol. 74, No. 3, Mar. 1985, pp. 348–350, American Pharmaceutical Association, Washington, DC, US, A.G. Bosanquet: "Stability of Melphalan Solutions During Preparation and Storage".
Chem. Abst., vol. 79, No. 14, Oct. 8, 1973, p. 324, Abst. 83438d, V. P. Safonov, et al., "Hydrolysis of Sarcolysin in Aqueous Solutions of Some High-Molecular-Weight Compounds and in Hydrochloric Acid Solutions".

Primary Examiner—Thurman K. Page
Attorney, Agent, or Firm—Donald Brown

[57] ABSTRACT

The present invention relates to a new two-component pharmaceutical formulation of melphalan in which the two components comprise
(a) freeze-dried mephalan hydrochloride and
(b) a solvent-diluent comprising a citrate, propylene glycol and ethanol.

Substantially pure melphalan, substantially pure melphalan hydrochloride and methods for preparing them are also described.

16 Claims, No Drawings

PHARMACEUTICAL FORMULATIONS

The present invention relates to novel pharmaceutical formulations, in particular to formulations containing melphalan as the active ingredient.

Melphalan is a well-established cytotoxic agent which is used to treat a range of neoplastic diseases, including in particular multiple myeloma and ovarian cancer.

Melphalan has the chemical name 4.[bis(2.chloroethyl)amino]-L-phenylalanine and the structural formula:

This compound is also known variously as L-phenylalanine mustard; L-PAM; L-sarcolysine; NSC-8806 and CB3025.

Melphalan is presently commercially available under the name Alkeran (TM. The Wellcome Foundation Limited) in the form of both tablets and injectable preparations. Alkeran injection is supplied as a three component presentation and has to be reconstituted in two stages, shortly prior to use. Thus, the three component system comprises a vial containing melphalan, as a powder, an ampoule containing an acid/alcohol solvent and an ampoule containing a phosphate buffer diluent, together with propylene glycol. To reconstitute the Alkeran injection, the melphalan powder is first dissolved in the acid/alcohol solvent and when dissolution is complete the solution is then neutralized and adjusted to the required concentration by addition of the diluent. This three-component system and the consequent two-step reconstitution procedure is clearly somewhat inconvenient and it would therefore be desirable to have available an injectable formulation which is simpler to reconstitute and thus more convenient for the physician to use. A further disadvantage of the presently available injectable formulation is that in some instances the melphalan powder dissolves only slowly or does not completely dissolve.

The present invention provides a novel two-component injectable melphalan preparation which overcomes the disadvantages of the currently available formulation.

In a first aspect the present invention provides an injectable formulation of melphalan comprising as two separate components (a) freeze-dried melphalan hydrochloride; and
(b) a solvent-diluent comprising a citrate, propylene glycol and ethanol.

Component (a) may advantageously include a non-hydroxylated matrix-forming agent, such as polyvinylpyrrolidone (PVP). A suitable grade of PVP for use in the formulation according to the invention comprises PVP having a molecular weight of less than 25,000, for example in the range 2,000 to 25.000. A particularly suitable grade of PVP is that designated K12.

The amount of melphalan hydrochloride present in component (a) may vary within wide limits and may constitute for example 1 to 99% by weight of component (a). Advantageously the melphalan hydrochloride comprises 5 to 80% by weight of component (a). When a matrix-forming agent is present the amount of matrix-forming agent may also vary within wide limits and may for example constitute between 0.1 and 99% by weight of component (a). Preferably however the amount of matrix forming agent is in the range 20 to 95% by weight of component (a), In component (b), the citrate may be an alkali metal citrate, e.g. potassium or preferably sodium citrate. The amount of propylene glycol in component (b) is generally in the range 40 to 80% by volume. The proportion of ethanol present in component (b) will generally be in the range 0.1 to 10% by volume. The citrate will generally comprise from 0.05 to 5% w/v e.g. 1.5 to 2.5% w/v of the solvent-diluent.

Component (a) may be prepared using freeze-drying procedures well known to those skilled in the art of pharmaceutical formulation. Thus, for example the melphalan base and the matrix forming agent may be dissolved in aqueous hydrochloric acid, the resulting solution sterilized by aseptic filtration, filled into sterile vials and freeze dried. The melphalan base and hydrochloric acid may be used in a stoichmetric (1:1) ratio, but preferably a slight excess of hydrochloric acid is used. Alternatively melphalan hydrochloride itself may advantageously be used to prepare the freeze dried component. In this case the hydrochloride may simply be dissolved in Water for Injection together with the matrix forming agent. If necessary further hydrochloric acid may be added as required. It will be appreciated that in the preparation of the freeze dried component aqueous solutions will generally be prepared with Water for Injections to ensure the sterility of the product.

The preparation of component (a), which is obtained as a sterile product, is considerably simpler and more efficient (and hence more economical) than the preparation of sterile melphalan powder and the subsequent procedure of aseptically filling the powder into vials, which is required in the case of the currently available injectable melphalan formulation. The formulation according to the present invention thus has advantages in manufacturing terms, as well as in its use by physicians.

The solvent-diluent (component (b)) may be prepared by mixing together an aqueous solution of the citrate with the propylene glycol and ethanol, sterilizing the solution by aseptic filtration and filling into sterile ampoules or vials. The solvent-diluent may also be presented in pre-filled syringes. Again aqueous solutions are preferably prepared using Water for Injections, and the preparation is carried out under aseptic conditions. The freeze-dried melphalan hydrochloride in component (a) of the formulation according to the present invention can readily be reconstituted by the single step addition of the solvent-diluent component (b). It will be appreciated that the amount of melphalan hydrochloride in component (a) and volume of solvent-diluent in component (b) can be selected to provide the desired dose and concentration of melphalan in the reconstituted product. The concentration of melphalan in the final formulation suitably lies in the range 0.5 to 10 mg/ml. A suitable unit dose may contain from 1 to 100 mg of melphalan. Preferred unit doses of melphalan contain 10 to 50 mg of the active ingredient in component (a). The volume of solvent diluent in component (b) may for example be from 1 to 50 ml, e.g. 5 to 25 ml, preferably 10 ml. Particularly preferred formulations according to the present invention are those in which component (a) contains 10 or 50 mg of melphalan and component (b)

comprises 10 ml of the solvent/diluent, such that the final reconstituted formulations have concentrations of 1 mg/ml and 5 mg/ml respectively.

The melphalan starting material which is used for the preparation of component (a) of the present formulation may itself be prepared by any method known in the art for preparing melphalan. A preferred form of melphalan for use in the preparation of component (a) is melphalan hydrochloride, most preferably substantially pure melphalan hydrochloride (i.e. having a purity of 95% or above, preferably 97% or above, measured by high pressure liquid chromatography (HPLC)). Melphalan hydrochloride may be prepared in highly pure form by crystallization, for example from a C2.4 alkanol. This may conveniently be achieved by forming a suspension or slurry of melphalan in a mixture of a C2.4 alkanol, preferably ethanol, and hydrogen chloride, heating the mixture conveniently to reflux temperature and then cooling to about 0°, whereupon melPhalan hydrochloride crystallizes out. In order to minimize the level of impurities, it is preferred that the duration of heating should be kept to a minimum, e.g. less than 5 minutes, preferably 1 to 3 minutes. In order to achieve this, a continuous crystallization process may be operated in which the suspension is formed at a temperature of 10°-20°C., is then passed through a heated vessel e.g. a heated coil, and finally collected and cooled.

Alternatively the substantially pure hydrochloride may be prepared from substantially pure melphalan, which may itself ba prepared by reacting ethyl N-phthaloyl-p-amino-L-phenylalanine or an acid addition salt thereof with ethylene oxide, such that the reaction temperature does not exceed 35° C., and preferably is in the range 20° to 30° C., followed by the steps of chlorination and hydrolysis, which may be carried out in conventional manner, to produce melphalan, which can then be converted into the hydrochloride salt in known manner. We have found the temperature during the reaction with ethylene oxide is critical to the purity of the final product and hence must be carefully controlled. As the reaction with ethylene oxide is exothermic the temperature can, if not controlled, rise considerably, for example up to 80° C.

Controlling the temperature in the range 20° to 30° C. also has the advantage of permitting a reduction in the amount ethylene oxide employed and thus results in an environmentally favorable process.

The formulations according to the present invention may be used to treat a variety of neoplastic conditions in analogous manner to the currently available injectable melphalan preparations. Thus for example the formulations may be used in the treatment of localized malignant melanoma and localized soft tissue sarcoma of the extremities, by regional perfusion. The formulations may also be used in the treatment of relapsed acute myeloid leukaemia, ovarian carcinoma, malignant melanoma, and multiple myeloma.

The dose of melphalan to be administered via the formulations of the present invention will depend upon the nature and severity of the conditions to be treated. In general the dosage schedules to be followed may be similar to those currently used for intravenous melphalan formulations. A variety of dosages schedules have been described in the literature. Thus, for example in the treatment of ovarian carcinoma a single intravenous infusion of 1 mg/kg bodyweight over 8 hours may be given every 4 weeks. High doses of melphalan (e.g. 140-200 mg/m$^2$) administered intravenously, may be used with or without autologous bone marrow transplantation, in the treatment of relapsed acute myeloid leukaemia, ovarian carcinoma, malignant melanoma and multiple myeloma. Low intravenous doses of melphalan (e.g. 16 mg/m$^2$) every 2 weeks for four doses and monthly thereafter may also be used.

The formulations according to the present invention will now be illustrated by the following non-limiting examples:

EXAMPLE 1

| Component (a) | |
|---|---|
| Ingredients | content per vial |
| Melphalan BP | 50.0 mg |
| Hydrochloric Acid, BP/Ph Eur | 34.5 μl |
| Povidone BP* | 20.0 mg |
| Water for Injections, BP/Ph Eur to | 2.0 g |

*polyvinylpyrrolidone

METHOD

Prepare a suitable dilution of the Hydrochloric Acid in Water for Injections. Add the Melphalan to part of the Water for Injections. Add the Hydrochloric Acid solution and stir until solution is complete. Add and dissolve the Povidone. Make up to weight with Water for Injections. Sterilize the solution by aseptic filtration. Fill into sterile vials. Freeze dry. Close and seal the vials.

| Component (b) | |
|---|---|
| Ingredients | content per vial |
| Sodium Citrate BP/Ph Eur | 0.2 g |
| Propylene Gylcol BP/Ph Eur | 6.0 ml |
| Ethanol (96%) BP | 0.52 ml |
| Water for Injections BP/Ph Eur to | 10.0 ml |

METHOD

Dissolve the Sodium Citrate in part of the Water for Injections. Add a mixture of the Propylene Glycol and Ethanol. Make up to volume with Water for Injections. Sterilize the solution by aseptic filtration. Fill into sterile ampoules or vials. Stopper with sterile closures and secure with aluminium collars.

Addition of component (b) to component (a) rapidly reconstitutes the freeze dried product to yield a solution for injection in the pH range 6 to 7.5.

EXAMPLE 2

| Component (a) | |
|---|---|
| Ingredients | content per vial |
| Melphalan BP | 10.0 mg |
| Hydrochloric Acid, BP/Ph Eur | 25.875 μl |
| Povidone BP | 90.0 mg |
| Water for Injections, BP/Ph Eur to | 1.5 g |

METHOD

The freeze-dried melphalan hydrochloride is prepared as described in Example 1.

Component (b)

The solvent-diluent is prepared as described in Example 1.

EXAMPLE 3

Preparation of substantially pure melphalan hydrochloride

A suspension of melphalan (2.0 kg) was stirred in 0.36 M ethanolic hydrogen chloride solution (18.0 liters) and then passed through a heated coil over a period CA.2 minutes to give a clear solution, which was continuously filtered on dischange from the coil. The filtrate was stirred at 0–5 degrees centigrade for 18 hours. The solid which crystallized was filtered, washed with diethylether, and dried at 30°–40°0 C. in vacuo to yield melphalan hydrochloride (1586g, 71%).

Purity (HPLC) 97.5%.

Analysis calculated for $C_{13}H_{19}O_2N_2Cl_3$: C 45.7%; H 5,6%; N 8.2%; Cl 31.13%; Found: C 45.82%; H 5.37%; N 8.06%; Cl 31.08%

An infra-red spectrum was obtained which was consistent with the structure of melphalan hydrochloride.

EXAMPLE 4

Substantially Pure Melphalan N-Phtaloyl-P-Amino-L-Phenylalanine Ethyl Ester Hydrochloride 187.25 g, 0.5 mole) was dissolved in a mixture of glacial acetic acid (205 ml) and water (205 ml), with stirring, ethylene oxide (83.0 g, 1.9 moles) was added slowly at 20–30 degrees centigrade, with cooling, then the solution stirred overnight at 20–30 degrees centigrade. The excess ethylene oxide was removed by stirring the solution in vacuo for 1 hour, then benzene (700 ml) and water (950 ml) were added. The acetic acid was neutralized by the addition of sodium bicarbonate (280 g), and the aqueous phase separated and extracted with benzene (2×140 ml). The benzene solutions were combined, washed with water (2×140 ml) and dried by distillation. Phosphorus oxychloride (600 g, 3.9 moles) was added slowly to the benzene solution, whilst stirring under reflux, the reaction mixture stirred under reflux for a further hour, then evaporated to dryness at 60 degrees centigrade in vacuo. The residue was dissolved in a mixture of butan-1-OL (625 ml) and ethanol (155 ml) at 80 degrees centigrade, and the solution was cooled to 10 degrees centigrade until the product crystallized.

The N,N-P-DI (2-chloroethyl)-amino-N'-Phthaloyl-L-Phenylalanine Ethyl Ester Hydrochloride was filtered, stirred as a suspension in diethyl ether (625 ml), filtered, washed with diethyl ether (340 ml) and dried at 20 degrees centigrade in vacuo to afford a white solid (167.48 67%). The chloroethyl compound was added to concentrated hydrochloric acid (840 ml), and the mixture stirred under reflux for 5 hours, cooled to 20 degrees centigrade and filtered. The aqueous solution was evaporated to dryness in vacuo and the residue dissolved in methanol (840 ml). Melphalan was precipitated by the addition of diethylamine (CA 90 ml) at 5–10 degree centigrade until the final suspension was at PH7. The melphalan was filtered, washed thoroughly with methanol (100 ml) and dried at 30–40 degrees centigrade in vacuo to afford the title compound as a white solid (68.28, 66%).

Purity (HPLC) 97.3%.

. 1 . A813.US

We claim:

1. A pharmaceutical formulation of melphalan comprising as two separate components
   (a) freeze-dried melphalan hydrochloride, and
   (b) a solvent-diluent comprising a citrate, propylene glycol and ethanol.

2. A pharmaceutical formulation according to claim 1 wherein component (a) includes a non-hydroxylated matrix-forming agent.

3. A pharmaceutical formulation according to claim 2 wherein the non-hydroxylated matrix-forming agent is polyvinylpyrrolidone.

4. A pharmaceutical formulation according to claim 1 wherein the citrate is an alkali metal citrate.

5. A method for preparing a pharmaceutical formulation of melphalan which comprises formulating as two separate components
   (a) freeze-dried melphalan hydrochloride and
   (b) a solvent-diluent comprising a citrate, propylene glycol and ethanol.

6. A pharmaceutical formulation according to claim 1, wherein the melphalan hydrochloride is in substantially pure form.

7. A pharmaceutical formulation according to claim 6, wherein the substantially pure melphalan hydrochloride is prepared by heating a mixture of melphalan and hydrogen chloride in a $C_{2-4}$ alkanol for up to five minutes and cooling to effect crystallization of melphalan hydrochloride.

8. A pharmaceutical formulation according to claim 6, wherein the melphalan hydrochloride is prepared by reacting ethyl N-phthaloyl-p-amino-L-phenylalnine or an acid addition salt thereof with ethylene oxide such that the reaction temperature does not exceed 35° C. followed by the steps of chlorination and hydrolysis and conversion into the hydrochloride salt.

9. A pharmaceutical formulation according to either claim 2 or claim 3, wherein the matrix-forming agent constitutes 20–95% by weight of component (a).

10. A pharmaceutical formulation according to claim 4, wherein the alkali metal citrate is selected from sodium and potassium citrate.

11. A pharmaceutical formulation according to claim 1, wherein component (b) contains 40–80% by volume of propylene glycol.

12. A pharmaceutical formulation according to claim 1, wherein component (b) contains 0.1–10% by volume of ethanol.

13. A pharmaceutical formulation according to claim 1, wherein component (b) contains 0.05–5% w/v of the citrate.

14. A pharmaceutical formulation according to claim 1, in the form of a unit dose containing from 1–100 mg of melphalan and from 1–50 ml of solvent-diluent.

15. A pharmaceutical formulation according to claim 14, containing 10 mg of melphalan and 10 ml of solvent-diluent.

16. A pharmaceutical formulation according to claim 14, containing 50 mg of melphalan and 10 ml of the solvent-diluent.

* * * * *